United States Patent

Beger et al.

[11] Patent Number: 5,902,305
[45] Date of Patent: May 11, 1999

[54] SURGICAL TENSIONING DEVICE

[75] Inventors: Jens Beger, Tuttlingen; Joachim Pfeil, Wiesbaden, both of Germany

[73] Assignee: Aesculap AG & Co. KG, Tuttlingen, Germany

[21] Appl. No.: 08/891,146

[22] Filed: Jul. 10, 1997

[30] Foreign Application Priority Data

Jul. 11, 1996 [DE] Germany .......................... 196 27 864

[51] Int. Cl.⁶ .................................................. A61B 17/56
[52] U.S. Cl. .......................................................... 606/103
[58] Field of Search ................................ 606/74, 72, 60, 606/86, 103

[56] References Cited

U.S. PATENT DOCUMENTS

| | | | |
|---|---|---|---|
| 4,966,600 | 10/1990 | Songer et al. . | |
| 5,057,113 | 10/1991 | Mingozzi . | |
| 5,116,340 | 5/1992 | Songer et al. . | |
| 5,312,410 | 5/1994 | Miller et al. . | |
| 5,569,253 | 10/1996 | Farris et al. | 606/74 |
| 5,609,596 | 3/1997 | Pepper | 606/103 |
| 5,693,046 | 12/1997 | Songer et al. | 606/74 |

FOREIGN PATENT DOCUMENTS

| | | |
|---|---|---|
| 532 698 | 8/1931 | Germany . |
| 933 289 | 8/1955 | Germany . |
| 19 58 429 | 7/1971 | Germany . |
| WO 95/05127 | 2/1995 | WIPO . |
| WO 95/06438 | 3/1995 | WIPO . |
| WO 95/22294 | 8/1995 | WIPO . |

*Primary Examiner*—Guy V. Tucker
*Attorney, Agent, or Firm*—Barry R. Lipsitz; Ralph F. Hoppin

[57] ABSTRACT

A surgical tensioning device for tensioning a tensioning element, such as a cable, that secures bone elements in position. The device includes a handle, a slide housed within the handle, and a holding element that is held on the slide. The slide is movable back and forth in a tensioning direction and contrary to the tensioning direction. The holding element secures the tensioning element on the slide during a movement of the slide in the tensioning direction. During a movement of the slide contrary to the tensioning direction, a blocking element held on the handle blocks a movement of the tensioning element contrary to the tensioning direction, and the holding element releases the tensioning element. The device is easily handled, and the tensioning of the tensioning element is not limited by the path of displacement of the slide.

23 Claims, 4 Drawing Sheets

SURGICAL TENSIONING DEVICE

BACKGROUND OF THE INVENTION

The invention relates to a surgical tensioning device for tensioning a tensioning means securing bone elements in position, comprising a handle and a slide which is movable back and forth in tensioning direction and on which a holding element securing the tensioning means on the slide during a movement of the slide in tensioning direction is held.

Tensioning devices of this type are used, in particular, with the application of so-called cerclage devices, with the aid of which the bone elements to be secured in position, for example, during the repositioning of oblique fractures are wrapped around by a tensioning means, for example a metal strap or a wire cable, and subsequently connected to one another and secured in position by tensioning the tensioning means. The cerclage devices are customarily premanufactured such that a first end of, for example, a wire cable is fixed to a cerclage locking member and the second, free end of the wire cable can be guided around the bone elements to be fixed in position, thereby forming a loop, and subsequently through a through bore in the cerclage locking member. With the aid of the tensioning device, the wire cable can subsequently be tensioned, wherein the housing of the tensioning device is supported on the cerclage locking member.

Surgical tensioning devices are known from U.S. Pat. Nos. specifications 5,116,340 and 4,966,600, in which the wire cable is tensioned by winding around a capstan. The capstan is held for rotation on a handle of a pair of pliers attachable to the cerclage locking member. In order to tension the wire cable, the mouth of the pliers must be clamped to the cerclage locking member and the free end of the wire cable subsequently threaded into the capstan, onto which the wire cable is then wound by turning a handle. The handling of this surgical tensioning device is thus rather complicated.

A difficult and time-consuming handling is a great disadvantage, in particular, when a larger number of cerclage devices are utilized during an operation and these are first of all fixed in position only temporarily in order to be able to subsequently correct the position of the bone elements to be fixed in position with cerclage devices which have already been applied. This operating technique is used, for example, in the field of spine surgery. In order to be able to carry out a correction of the spine by tensioning the cerclage devices, an intraoperative, temporary fixing in position of the cerclage devices must be possible which allows subsequent tensioning and correction. As a result, the surgical tensioning device must often be reapplied to the loose ends of the wire cable. The use of a capstan for winding and tensioning the wire cable results in a time-consuming operating technique.

Tensioning devices with two telescoping housing sections are known (U.S. Pat. No. 5,312,410, Wo 95/22294), wherein a first housing section can be supported on the cerclage locking member and a second housing section is displaceable in tensioning direction. The free end of the wire cable is guided axially through the tensioning device and secured on the second housing section. A construction of this type has, in particular, the disadvantage that the wire cable can be tensioned only to such an extent until the maximum path of displacement of the second housing section has been reached.

Finally, surgical tensioning devices are also known (U.S. Pat. No. 5,057,113, WO 95/05127), in which a slide, which is displaceable in tensioning direction and to which the free end of the wire cable can be secured by means of a holding element, is used instead of two telescoping housing sections. The holding element is designed such that the wire cable is fixed in position on the slide during a movement of the slide in tensioning direction. These tensioning devices are also subject to the disadvantage described above that the tensioning of the wire cable which can be achieved is limited to the path of displacement of the slide.

SUMMARY OF THE INVENTION

The object of the present invention is to design a surgical tensioning device of the type specified at the outset such that it exhibits a simple handling and the tensioning of the tensioning means which can be achieved is not limited by the path of displacement of the slide.

This object is accomplished in accordance with the invention, in a surgical tensioning device of the generic type, in that a blocking element blocking a movement of the tensioning means contrary to the tensioning direction is held on the handle and that the holding element releases the tensioning means during a movement of the slide contrary to the tensioning direction.

With the aid of the slide movable in tensioning direction, the tensioning means can first of all be tensioned to such an extent until the slide has taken up its proximal position.

During this movement, the tensioning means is fixed in position on the slide by means of the holding element held on the slide; the tensioning means thus experiences a tractive force in tensioning direction. In order to be able to subsequently tension the tensioning means further, the slide must be brought into its distal position. In accordance with the invention, the tensioned tensioning means is released by the holding element during a movement of the slide contrary to the tensioning direction so that the slide can move independently of the tensioning means, and at the same time it is ensured as a result of the blocking element held on the handle that a movement of the tensioned tensioning means contrary to the tensioning direction is blocked. With the aid of the blocking element held on the handle it is thus ensured that the tensioning of the tensioning means achieved by the slide during its movement in tensioning direction is maintained during a subsequent movement of the slide contrary to the tensioning direction. If the slide has taken up its distal position, it can be moved again in tensioning direction, wherein it is ensured at the same time as a result of the action of the holding element that the tensioning means is fixed in position on the slide during such a movement of the slide in tensioning direction. The tensioning means can thus be tensioned further, wherein it is not affected by the blocking element held on the housing during the resulting movement in tensioning direction.

The inventive surgical tensioning device thus exhibits a simple handling since only the slide need be moved back and forth in tensioning direction in order to tension the tensioning means. With the aid of the holding element held on the slide it is ensured that the tensioning means is fixed reliably in position on the slide during a movement of the slide in tensioning direction and thus experiences a tractive force, and with the aid of the blocking element held on the handle it is ensured that the tensioning already achieved is maintained when the slide is moved contrary to the tensioning direction in order to exert a tractive force on the tensioning means again during a renewed movement in tensioning direction which subsequently takes place. The tensioning of the tensioning means which can be achieved is thus not limited by the path of displacement of the slide.

It is of advantage when the blocking element and/or the holding element comprise a friction locking mechanism. The use of a friction locking mechanism has the advantage that additional connecting means for securing the tensioning means are omitted since, in the case of a friction locking mechanism, the fixing in position of the tensioning means on the blocking and/or on the holding element takes place solely as a result of the frictional force between tensioning means and blocking or holding element.

In a particularly preferred development of the inventive surgical tensioning device it is provided for the blocking and/or the holding element to comprise a clamping element which is held on the handle or on the slide, clamps the tensioning means between itself and a corresponding contact surface during a movement contrary to the tensioning direction and releases the tensioning means during a movement in the opposite direction. In the case of such a design, the free end of the tensioning means is guided through between the clamping element and the corresponding contact surface. The clamping element acts as a friction locking mechanism which reliably prevents any movement of the tensioning means contrary to the tensioning direction since, on account of the friction between tensioning means and clamping element, the latter clamps the tensioning means between itself and the corresponding contact surface during a movement contrary to the tensioning direction. This means that a movement of the tensioning means contrary to the tensioning direction is reliably prevented. A movement of the tensioning means in tensioning direction is, however, possible at any time since the tensioning means is released by the clamping element during a movement directed in tensioning direction. The clamping element exerts a clamping force on the tensioning means only when the tensioning means moves contrary to the tensioning direction relative to the clamping element.

It is of advantage when the clamping element and the corresponding contact surface project laterally beyond the handle of the surgical tensioning device and the tensioning means can be inserted between clamping element and contact surface. Such a design results in a time-consuming threading of the tensioning means being omitted. Instead of this, the tensioning means can be inserted between clamping element and contact surface laterally on the handle. The repeated application of the surgical tensioning device and subsequent tensioning of the tensioning means required, in particular, during use in the field of spine surgery is thus simplified to a considerable extent.

An additional simplification of the inventive surgical tensioning device is achieved in an advantageous development in that the clamping element can be secured in a position spaced from the contact surface for the insertion of the tensioning means. On account of the distance between clamping element and contact surface, the insertion of the tensioning means is particularly easy. For this purpose, an adjusting mechanism can be provided which can be activated by means of an actuating element and during its actuation holds the clamping element in a position spaced from the contact surface. An actuating button or an actuating lever can, for example, be used as actuating element. The actuating element of the adjusting mechanism can be activated in the case of such a design for the purpose of introducing the tensioning means into the inventive surgical tensioning device. As a result, the clamping element takes up a position spaced from the contact surface and so the tensioning means can easily be inserted between clamping element and contact surface laterally on the handle. Clamping element and contact surface project laterally beyond the handle for this purpose. Subsequently, the adjusting mechanism is deactivated and, as a result, the clamping element takes up a position abutting on the tensioning means so that any movement of the tensioning means contrary to the tensioning direction is impeded on account of the frictional force between clamping element and tensioning means.

In an advantageous development it is provided for the clamping element to be pivotable between a first position releasing the tensioning means and a second position clamping the tensioning means. With such a design, the clamping element comprised by the blocking and/or holding element is held so as to be pivotable on the handle or on the slide and executes a pivoting movement directed towards the second, clamping position during a movement of the tensioning means contrary to the tensioning direction on account of the frictional force between clamping element and tensioning means and so the tensioning means is clamped between the clamping element and the corresponding contact surface.

It is of advantage when the clamping element is elastically pretensioned in the direction towards its second position. As a result, the clamping element blocks any movement of the tensioning means contrary to the tensioning direction without delay, i.e. the tensioning means is prevented first of all from carrying out any limited movement directed contrary to the tensioning direction until the clamping element takes up its second, clamping position. On account of the elastic pretensioning, the clamping element is automatically pivoted to such an extent in the direction towards its clamping position that each movement of the tensioning means contrary to the tensioning direction is practically prohibited without delay. The elastic pretensioning exerted, for example, by a helical or spiral spring has no influence on the holding force exerted by the clamping element on the tensioning means since the tensioning means is clamped between the clamping element and the corresponding contact surface in a self-locking manner.

In an embodiment of the inventive surgical tensioning device which can be produced inexpensively it is provided for the clamping element to be designed as an eccentrically mounted, for example, cylindrical friction roller.

In a particularly preferred development it is provided for the blocking and/or holding element to each have two clamping elements which interact with one another, clamp the tensioning means between them during a movement contrary to the tensioning direction and release the tensioning means during a movement in the opposite direction and which are respectively held on the handle or on the slide. With such a design, the contact surface corresponding to a clamping element is thus formed by the second clamping element. The two clamping elements accommodate the tensioning means between them and each exert a clamping force on the tensioning means during a movement of the tensioning means contrary to the tensioning direction. The clamping force exerted altogether by the blocking and/or holding element is thus augmented.

In an advantageous development, it is provided for the slide to be arranged so as to be displaceable back and forth in tensioning direction within a housing. The housing can form a guide means for the slide which is displaceable between its distal position close to the front end of the housing and its proximal position adjacent the rear end of the housing.

The slide can be designed, for example, as a piston guided in a section of the housing in the shape of a hollow cylinder.

It is of advantage for a simple handling of the surgical tensioning device when the handle is arranged on the outer side of the housing.

In a preferred development, the slide can be displaced back and forth in tensioning direction by actuating a pivot lever arranged on the handle. In order to tension the tensioning means, only the pivot lever need, therefore, be actuated so that the slide is displaced back and forth in tensioning direction within the housing, wherein it exerts a respective tractive force on the tensioning means during a movement in tensioning direction.

The slide can be connected to the pivot lever in an advantageous manner via a lever mechanism.

It is particularly advantageous when the slide can be moved in tensioning direction contrary to the action of an elastic return force. As a result of the elastic return force, it is ensured that the slide automatically takes up its front, distal position. The handling of the surgical tensioning means is considerably simplified by this. The slide can, for example, as described above, be moved by means of a pivot lever. For acting on the slide with an elastic return force a leaf spring can be provided which presses the pivot lever into a position projecting from the housing. The elastic return force acting on the pivot lever is advantageously transferred to the slide via the lever mechanism. In order to tension the tensioning means, the slide must therefore be moved out of its distal into its proximal position. The movement in the opposite direction is then brought about automatically due to the action of the elastic return force.

The following description of a preferred embodiment of the invention serves to explain the invention in greater detail in conjunction with the drawings.

DETAILED DESCRIPTION OF THE INVENTION

Figure 1:
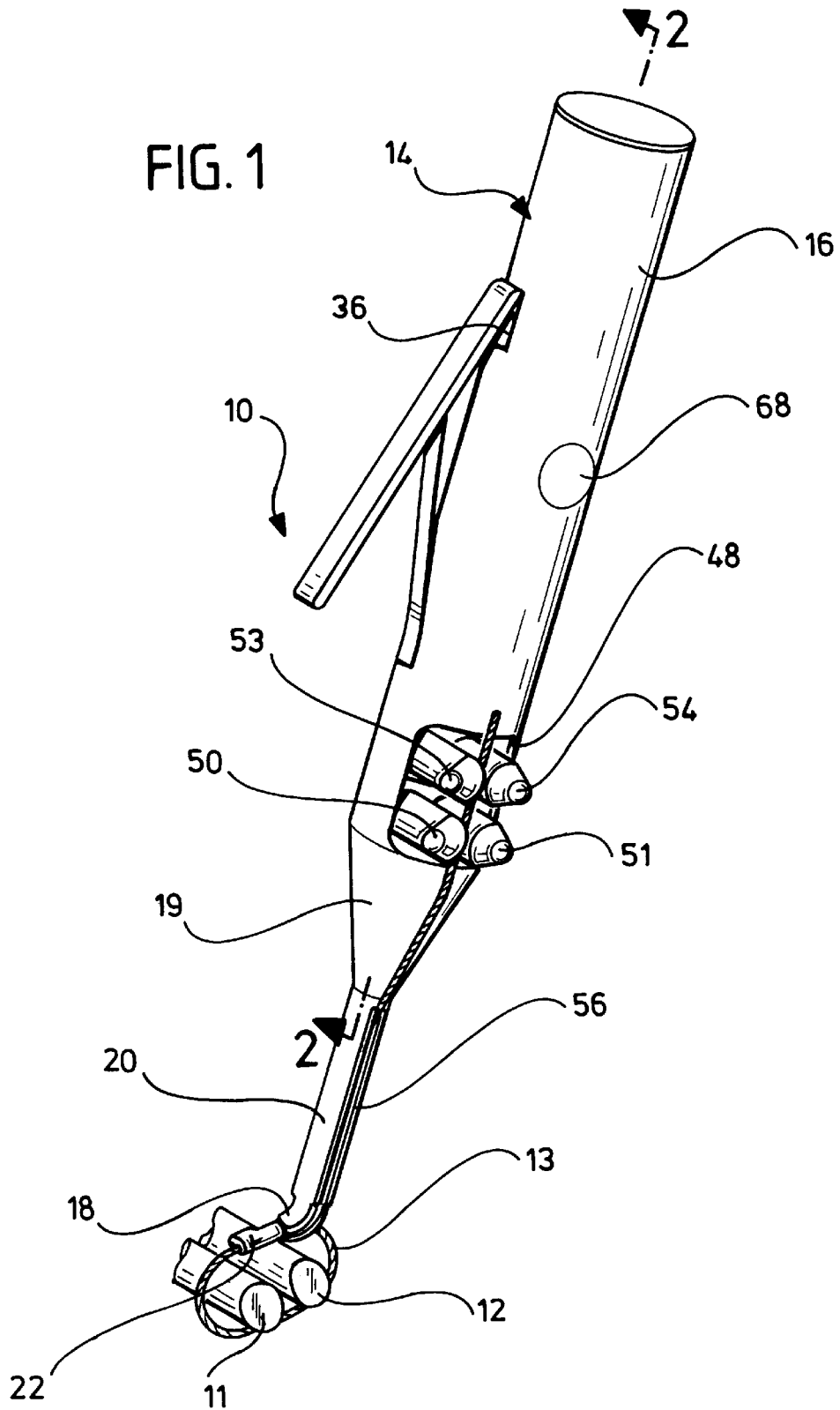
FIG. 1: shows a schematic, perspective illustration of an inventive surgical tensioning device.
Figure 2:
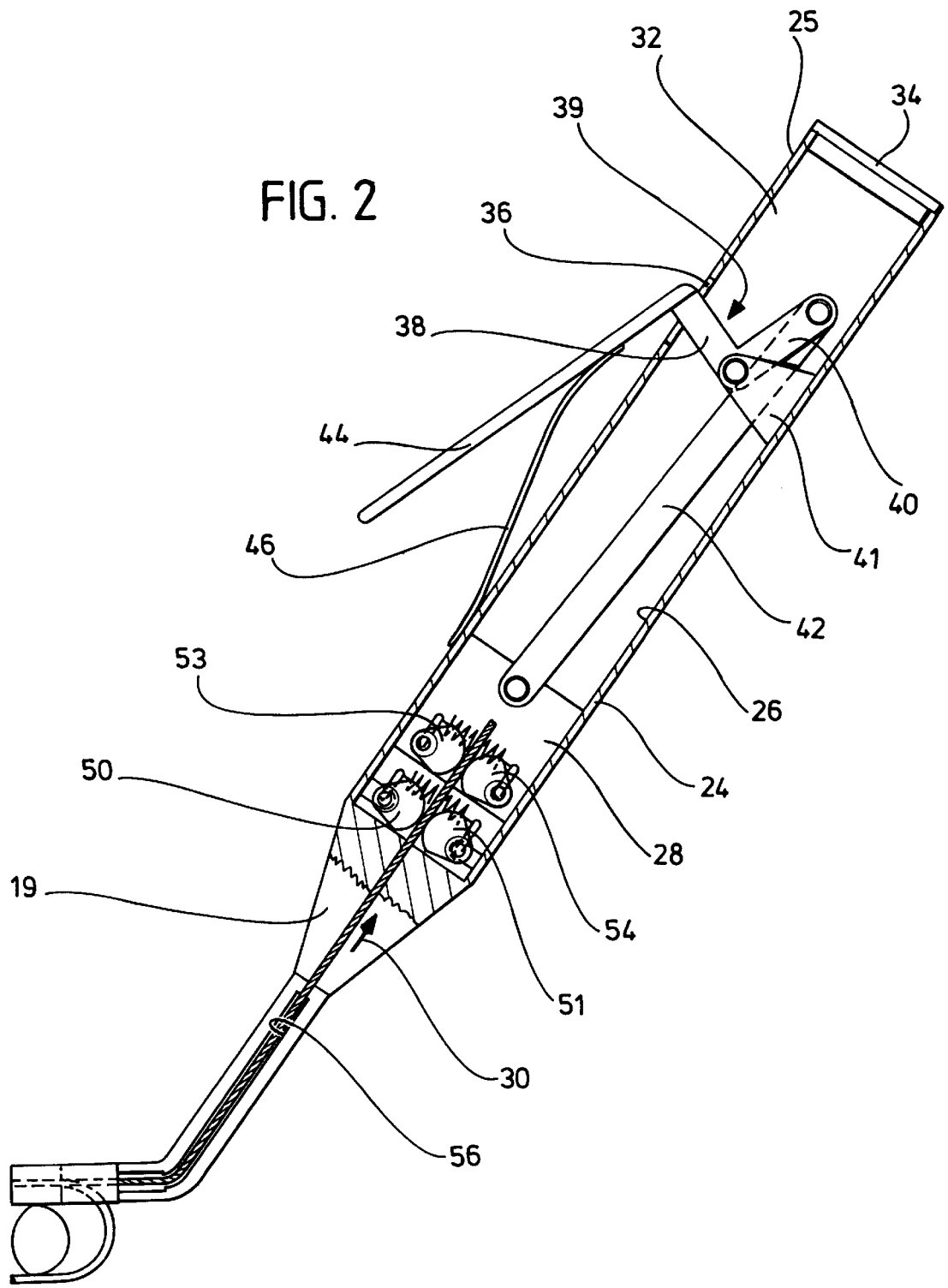
FIG. 2: shows a sectional view along line 2—2 in FIG. 1.

A surgical tensioning device provided as a whole with the reference numeral 10 is illustrated in FIGS. 1 and 2, with the aid of which a tensioning means in the form of a wire cable 13 surrounding two bone elements 11, 12 can be tensioned. The tensioning device 10 comprises a housing 14 which forms a handle 16 which merges at its distal end via a conical section 19 into a tip 20 angled at its distal end region 18. The distal end region 18 is designed to abut on a cerclage locking member 22 so that the surgical tensioning device 10 can be supported on the cerclage locking member 22 for tensioning the wire cable. The housing 14 designed in the form of a hollow cylinder with a circular base surface comprises a housing wall 24 which is designed as a cylinder casing and on the inner side 26 of which a slide 28 abuts so that the inner side 26 forms a guide means for the slide 28 which can be displaced back and forth in tensioning direction along the inner side 26. The tensioning direction is symbolized in FIG. 2 by the arrow 30.

The interior 32 enclosed by the housing wall 24 is sealed at the proximal end of the housing 14 by a threaded plug 34 and is accessible, for example, for sterilization of the tensioning device 10 after removal of the plug 34. The housing wall 24 has a slot 36 which extends in axial direction and has a first end region 38 of an elbow lever 39 passing through it, at the second end region 40 of which facing the proximal end of the housing 14 a connecting rod 42 rotatably held on the slide 28 is articulatedly connected. The elbow lever 39 is rotatably mounted on a bearing block 41 secured to the inner side 26 of the housing wall 24. A pivot lever 44 is arranged at the first end region 38 of the elbow lever 39, which projects slightly beyond an outer side 25 of the housing wall 24, and is acted upon by a leaf spring 46 held at the outer side 25 with an elastic return force acting essentially radially outwards.

If the pivot lever 44 is pivoted in the direction towards the outer side 25 of the housing wall 24 contrary to the action of the leaf spring 46, the slide 28 is thereby displaced via the connecting rod 42 and the elbow lever 39 to such an extent intensioning direction until the pivot lever 44 is aligned essentially parallel to the outer side 25 of the housing wall 24. If the pivot lever 44 is subsequently no longer acted upon with a force directed towards the outer side 25, it automatically takes up its original position illustrated in FIG. 2 on account of the elastic return force exerted by the leaf spring 46, wherein the slide 28 is displaced at the same time contrary to the tensioning direction 30 in the direction towards the distal end of the housing 14 via the elbow lever 39 and the connecting rod 42. As a result of repeated actuation of the pivot lever 44, the slide 28 can thus be moved back and forth in tensioning direction 30.

In the region adjoining the conical section 19 of the housing 14 in tensioning direction 30, the housing wall 24 has an opening 48 which has front friction rollers 50 and 51 immediately adjacent the conical section 19 as well as rear friction rollers 53 and 54 arranged a t a distance from the conical section 19 passing through it. The front and rear friction rollers 50, 51 and 53, 54 are thus accessible at the outer side 25 of the housing wall 24. They accommodate the wire cable 13 between them which is guided in the region of the tip 20 in a longitudinal groove 56 extending in tensioning direction 30.

The region of the front and the rear friction rollers 50, 51 and 53, 54 is illustrated on a larger scale in FIGS. 3 to 6. The friction rollers 50, 51, 53, 54 are aligned respectively parallel to one another and at right angles to the tensioning direction 30. Both the front friction rollers 50, 51 and the rear friction rollers 53, 54 are respectively designed in the shape of a cylinder with a base surface essentially in the shape of a circular sector and are mounted eccentrically and so as to be pivotable on the inner side 26 of the housing 24 or on the slide 28. An arm 60, 61 and 63, 64 is non-rotatably held both on the respective front friction rollers 50, 51 and on the respective rear friction rollers 53, 54, wherein the arms 60, 61 of the front friction rollers like the arms 63, 64 of the rear friction rollers are respectively connected with one another by a helical spring 65 and 66, respectively, in their end regions facing away from the friction rollers 50, 51 and 53, 54.

Figure 3:
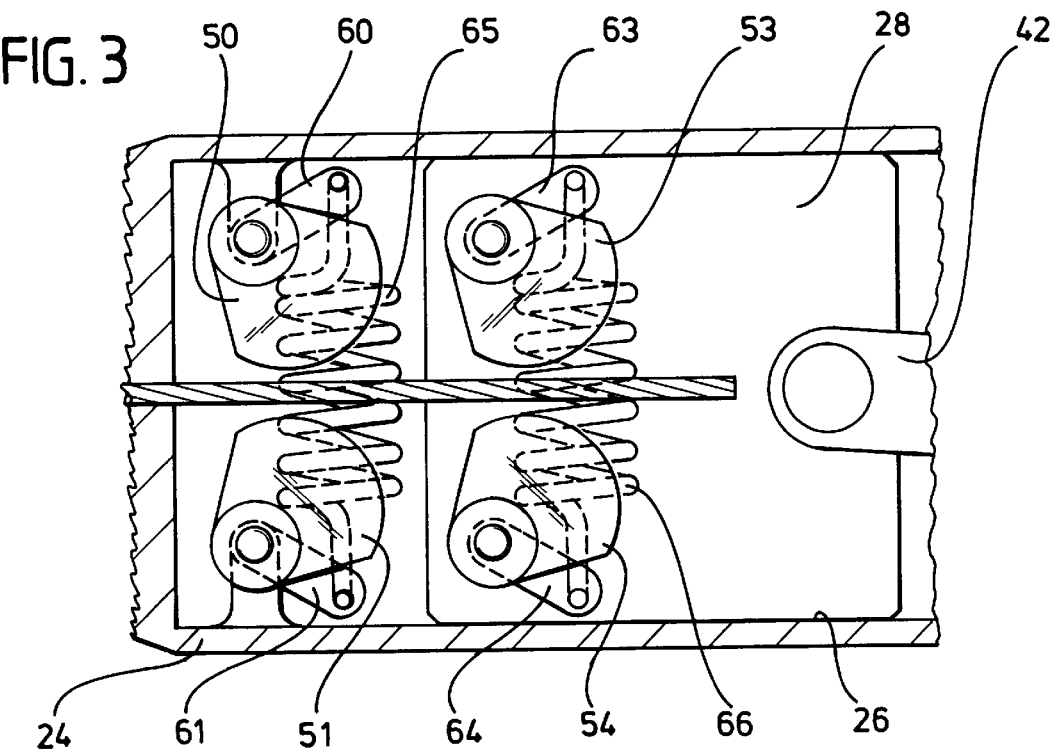
FIG. 3: shows an enlarged illustration of the sectional view according to FIG. 2 in the region of the blocking and the holding elements during the insertion of a tensioning means.
Figure 4:
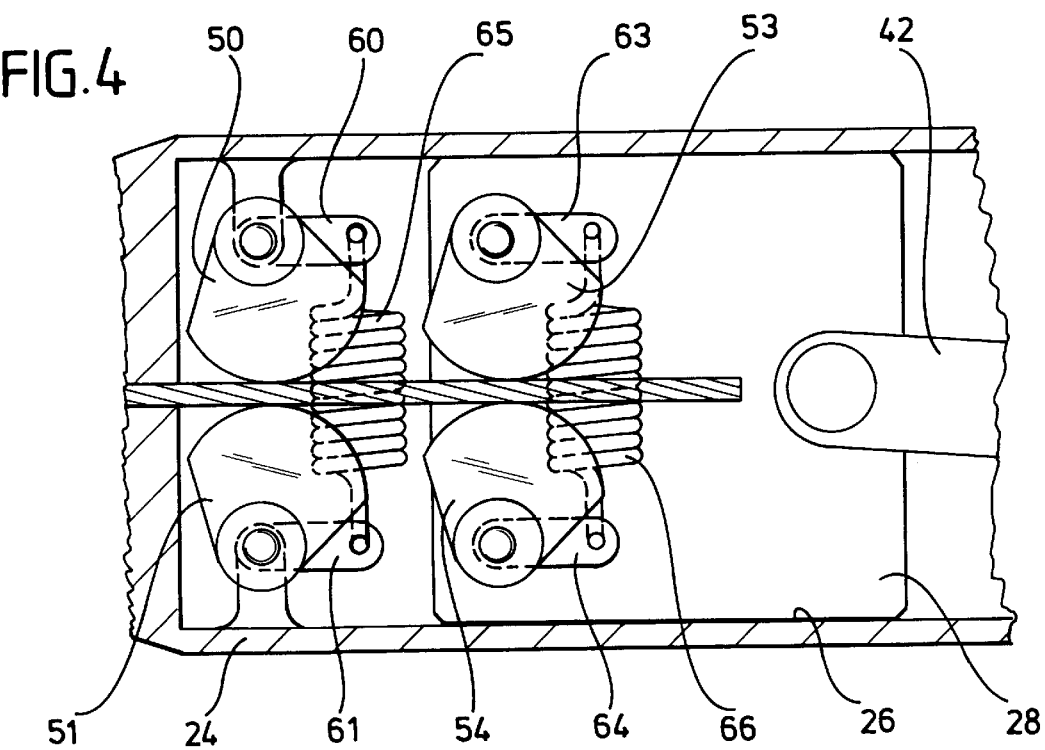
FIG. 4: shows an illustration according to FIG. 3 after successful insertion of the tensioning means.

The front and rear friction rollers 50, 51 and 53, 54 are pivotable between a releasing position illustrated in FIG. 3, in which they are arranged at a distance from the wire cable 13, and a clamping position illustrated in FIG. 4, in which they respectively abut on the wire cable 13 so that this is clamped not only between the front friction rollers 50 and 51 but also between the rear friction rollers 53 and 54. During the transition from their clamping position illustrated in FIG. 4 into their releasing position illustrated in FIG. 3 the friction rollers 50, 51, 53, 54 are each acted upon with an elastic return force acting in the direction towards the clamping position on account of the action of the helical springs 65 and 66, respectively.

As described above, the wire cable 13 can be inserted between the front friction rollers 50, 51 as well as between the rear friction rollers 53, 54 outside the housing 14. For this purpose, the surgical tensioning device 10 comprises an adjusting mechanism which is known per se but not illustrated in the drawings and which can be activated by means of an actuating button 68 arranged at the level of the pivot lever 44 and transfers the front and rear friction rollers 50, 51 and 53, 54 into their position releasing the wire cable 13 which is illustrated in FIG. 3. This means that the wire cable 13 can be inserted between the friction rollers without any additional aids. This insertion takes place at the same time as the actuating button 68 is pressed. After the insertion, the actuating button 68 is released so that not only the front friction rollers 50, 51 but also the rear friction rollers 53, 54 take up their position clamping the wire cable 13 on account of the elastic return force of the helical springs 65 and 66, respectively.

Figure 5:
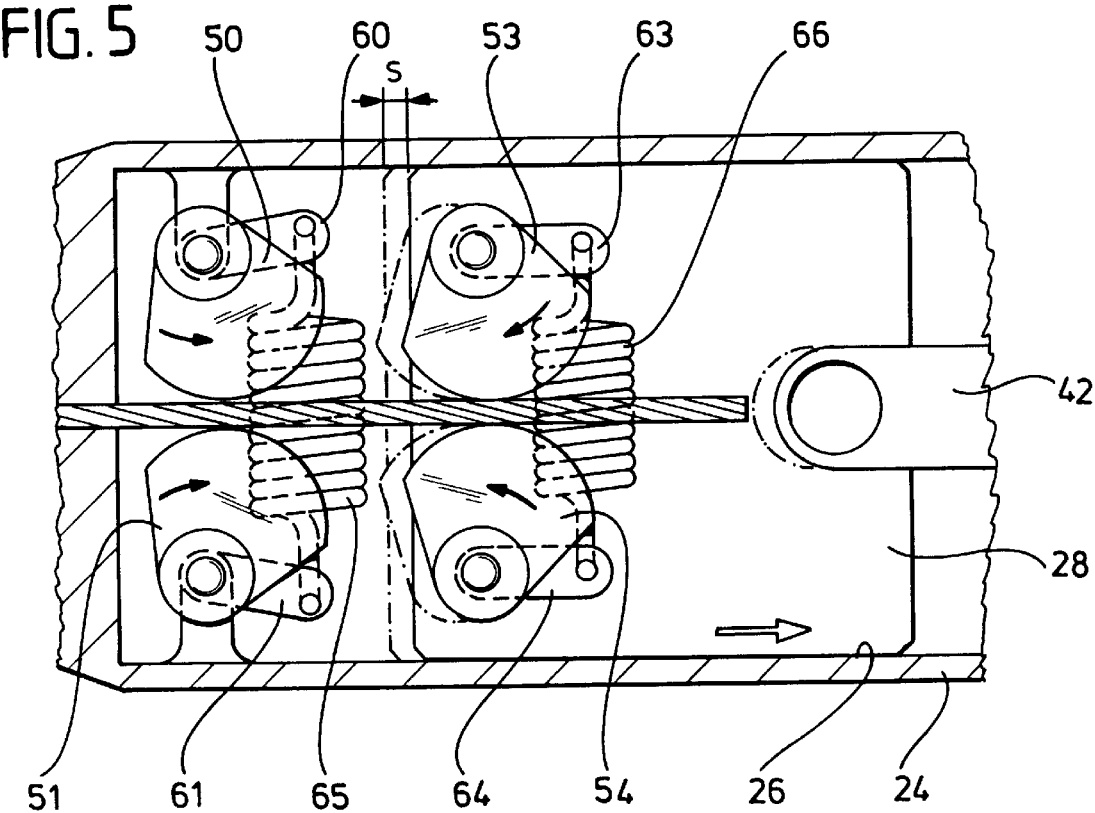
FIG. 5: shows an illustration according to FIG. 3 during displacement of the slide in tensioning direction
Figure 6:
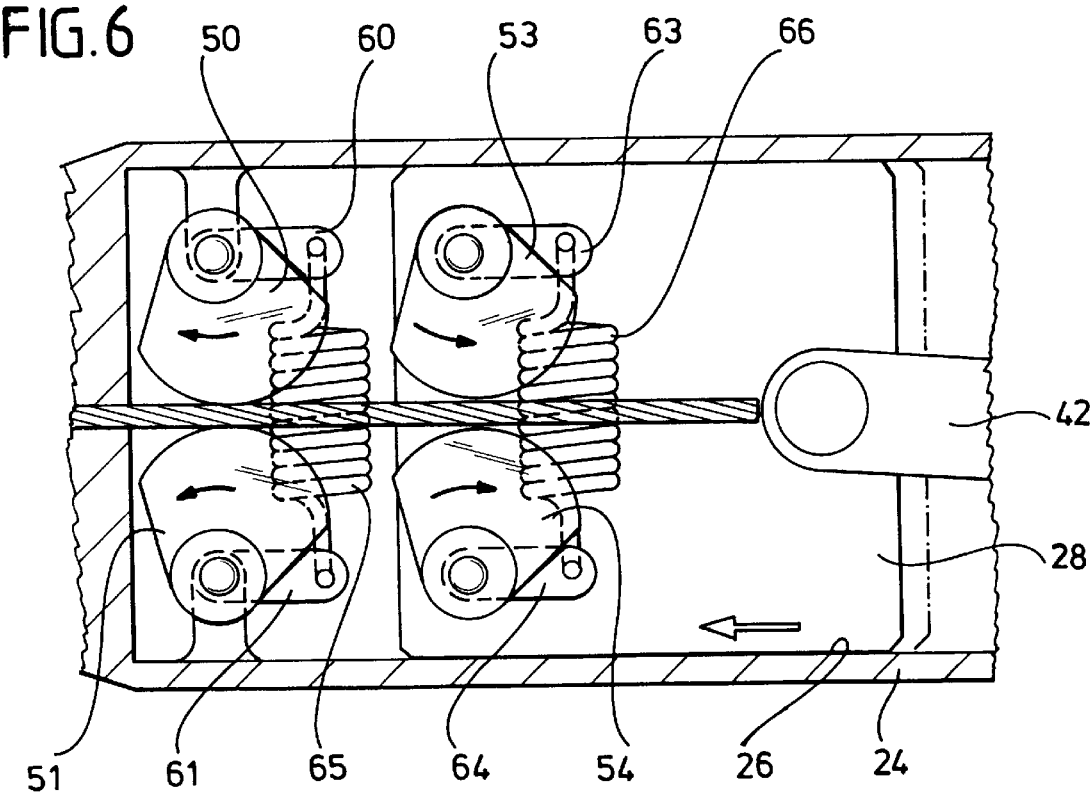
FIG. 6: shows an illustration according to FIG. 3 during displacement of the slide contrary to the tensioning direction.

If the pivot lever 44 is now actuated and thus the slide 28—as illustrated in FIG. 5—displaced in tensioning direction 30, this results in the front friction rollers 50, 51 being pivoted towards their position releasing the wire cable 13 on account of the friction between these rollers and the wire cable 13. In contrast thereto, the rear friction rollers 53, 54 which are held so as to be pivotable on the slide 28 and are displaced with it in tensioning direction 30 clamp the wire cable 13 between them. The wire cable 13 thus undergoes automatic locking at the rear friction rollers 53, 54 during displacement of the slide in tensioning direction 30 and so these rollers fix the wire cable 13 in position on the slide 28 so as to be non-displaceable. During actuation of the pivot lever 44, the wire cable 13 is thus tensioned in tensioning direction in that the wire cable 13 is drawn in tensioning direction through the path of displacement s illustrated in FIG. 5 when the slide 28 is displaced from its front position illustrated by dash-dot lines in FIG. 5 into its rear position illustrated by solid lines in FIG. 5 due to actuation of the pivot lever 44.

As described above, the slide 28 automatically takes up its front position again following actuation of the pivot lever 44 on account of the elastic return force exerted by the leaf spring 46, i.e. the slide 28 is displaced contrary to the tensioning direction 30. Such a return movement, illustrated in FIG. 6, results in the rear friction rollers 53, 54 being pivoted into their releasing position on account of the friction force between the friction rollers and the wire cable 13. A movement of the wire cable 13 contrary to the tensioning direction 30 is, however, reliably prevented during a return movement of the slide 28 due to the action of the front friction rollers 50, 51 since the front friction rollers 50, 51 clamp the wire cable 13 between them during a movement of the wire cable 13 contrary to the tensioning direction 30.

The front friction rollers 50, 51 thus form a blocking element which is held on the housing 14 of the surgical tensioning device 10 and blocks any movement of the wire cable 13 contrary to the tensioning direction but allows a movement of the wire cable 13 in the opposite direction at any time. The rear friction rollers 53, 54 ensure that the wire cable 13 is reliably fixed in position on the slide 28 during a movement of the slide 28 in tensioning direction 30 and is thus drawn further in tensioning direction 30 with the slide 28. During a movement of the slide 28 contrary to the tensioning direction 30 the rear friction rollers 53, 54 do, however, release the wire cable. Both the front friction rollers 50, 51 and the rear friction rollers 53, 54 respectively form a friction locking mechanism which reliably blocks any movement of the wire cable 13 contrary to the tensioning direction 30 without the use of additional aids.

As a result of an oscillating movement of the slide 28 the wire cable 13 is thus drawn further through the path of displacement s each time so that the desired tensioning of the wire cable 13 can be achieved without this being restricted by the path of displacements.

What is claimed is:

1. A surgical tensioning device for tensioning a tensioning means, said tensioning means adapted to secure bone elements in position, comprising:

a handle;

slide movable back and forth in a tensioning direction and contrary to said tensioning direction;

a holding element held on said slide;

said holding element adapted to secure the tensioning means on said slide during a movement of said slide in said tensioning direction; and a blocking element held on said handle; wherein:

said blocking element is adapted to block a movement of the tensioning means contrary to said tensioning direction; and said holding element is adapted to release the tensioning means during a movement of said slide contrary to said tensioning direction.

2. A surgical tensioning device as defined in claim 1, wherein said blocking element comprises:

a clamping element; wherein:

said clamping element is held on one of said handle and said slide;

said clamping element is adapted to clamp the tensioning means between said clamping element and a corresponding contact surface during said movement of said slide contrary to said tensioning direction; and said clamping element is adapted to release the tensioning means during said movement of said slide in said tensioning direction.

3. A surgical tensioning device as defined in claim 2, wherein:

said clamping element and said contact surface project laterally beyond said handle; and the tensioning means is adapted to be inserted between said clamping element and said contact surface.

4. A surgical tensioning device as defined in claim 2, wherein:

said clamping element is adapted to be secured in a position spaced from said contact surface.

5. A surgical tensioning device as defined in claim 2, wherein:

said clamping element is pivotable between (a) a first position, in which said clamping element is adapted to release the tensioning means, and (b) a second position, in which said clamping element is adapted to clamp the tensioning means.

6. A surgical tensioning device as defined in claim 5, wherein:

said clamping element is elastically pretensioned in the direction towards said second position.

7. A surgical tensioning device as defined in claim 2, wherein:
said clamping element comprises an eccentrically mounted friction roller.

8. A surgical tensioning device as defined in claim 1, wherein:
at least one of said blocking element and said holding element comprise a friction locking mechanism.

9. A surgical tensioning device as defined in claim 8, wherein said blocking element comprises:
a clamping element; wherein:
said clamping element is held on one of said handle and, said slide;
said clamping element is adapted to clamp the tensioning means between said clamping element and a corresponding contact surface during said movement of said slide contrary to said tensioning direction; and
said clamping element is adapted to release the tensioning means during said movement of said slide in said tensioning direction.

10. A surgical tensioning device as defined in claim 8, wherein said holding element comprises:
a clamping element; wherein:
said clamping element is held on one of said handle and said slide;
said clamping element is adapted to clamp the tensioning means between said clamping element and a corresponding contact surface during said movement of said slide in said tensioning direction; and
said clamping element is adapted to release the tensioning means during said movement of said slide contrary to said tensioning direction.

11. A surgical tensioning device as defined in claim 1, wherein said blocking element comprises:
two clamping elements interacting with one another; wherein:
said two clamping elements are adapted to clamp the tensioning means therebetween during said movement of said slide contrary to said tensioning direction;
said two clamping elements are adapted to release the tensioning means during said movement of said slide in said tensioning direction; and
said clamping elements are respectively held on one of said handle and said slide.

12. A surgical tensioning device as defined in claim 12, further comprising:
a housing in which said slide is movable back and forth in said tensioning direction and contrary to said tensioning direction.

13. A surgical tensioning device as defined in claim 12, wherein:
said housing comprises a hollow cylinder; and
said slide comprises a piston that is guided in said hollow cylinder.

14. A surgical tensioning device as defined in claim 1, further comprising:
a pivot lever arranged on said handle; wherein:
slide is displaceable back and forth in said tensioning direction and contrary to said tensioning direction by actuating said pivot lever.

15. A surgical tensioning device as defined in claim 14, further comprising:
a lever mechanism for connecting said slide to said pivot lever.

16. A surgical tensioning device as defined in claim 1, wherein:
said slide is movable in said tensioning direction contrary to the action of an elastic return force.

17. A surgical tensioning device as defined in claim 1, wherein said holding element comprises:
a clamping element; wherein:
said clamping element is held on one of said handle and said slide;
said clamping element is adapted to clamp the tensioning means between said clamping element and a corresponding contact surface during said movement of said slide in said tensioning direction; and
said clamping element is adapted to release the tensioning means during said movement of said slide contrary to said tensioning direction.

18. A surgical tensioning device as defined in claim 17, wherein:
said clamping element and said contact surface project laterally beyond said handle; and
the tensioning means is adapted to be inserted between said clamping element and said contact surface.

19. A surgical tensioning device as defined in claim 17, wherein:
said clamping element is adapted to be secured in a position spaced from said contact surface.

20. A surgical tensioning device as defined in claim 17, wherein:
said clamping element is pivotable between (a) a first position, in which said clamping element is adapted to release the tensioning means, and (b) a second position, in which said clamping element is adapted to clamp the tensioning means.

21. A surgical tensioning device as defined in claim 20, wherein:
said clamping element is elastically pretensioned in the direction towards said second position.

22. A surgical tensioning device as defined in claim 17, wherein:
said clamping element comprises an eccentrically mounted friction roller.

23. A surgical tensioning device as defined in claim 1, wherein said holding element comprises:
two clamping elements interacting with one another; wherein:
said two clamping elements are adapted to clamp the tensioning means therebetween during said movement of said slide in said tensioning direction;
said two clamping elements are adapted to release the tensioning means during said movement of said slide contrary to said tensioning direction; and
said clamping elements are respectively held on one of said handle and said slide.

* * * * *

UNITED STATES PATENT AND TRADEMARK OFFICE
CERTIFICATE OF CORRECTION

PATENT NO. : 5,902,305

DATED : 5/11/99

INVENTOR(S) : Beger et al.

It is certified that error appears in the above-identified patent and that said Letters Patent is hereby corrected as shown below:

Column 8, line 30, before "release" insert --automatically--

Signed and Sealed this

Thirty-first Day of October, 2000

Attest:

Q. TODD DICKINSON

*Attesting Officer*      *Director of Patents and Trademarks*